(12) United States Patent
Chewter et al.

(10) Patent No.: US 9,120,069 B2
(45) Date of Patent: Sep. 1, 2015

(54) PROCESS AND REACTOR SYSTEM FOR THE PREPARATION OF AN OLEFINIC PRODUCT

(75) Inventors: Leslie Andrew Chewter, Amsterdam (NL); Jeroen Van Westrenen, Amsterdam (NL); Ferry Winter, Amsterdam (NL)

(73) Assignee: Shell Oil Company, Houston, TX (US)

( * ) Notice: Subject to any disclaimer, the term of this patent is extended or adjusted under 35 U.S.C. 154(b) by 864 days.

(21) Appl. No.: 13/140,933

(22) PCT Filed: Dec. 21, 2009

(86) PCT No.: PCT/EP2009/067625
§ 371 (c)(1),
(2), (4) Date: Jul. 19, 2011

(87) PCT Pub. No.: WO2010/072706
PCT Pub. Date: Jul. 1, 2010

(65) Prior Publication Data
US 2012/0108876 A1 May 3, 2012

(30) Foreign Application Priority Data
Dec. 22, 2008 (EP) .................................... 08172550

(51) Int. Cl.
| | | |
|---|---|---|
| *C01C 1/20* | (2006.01) | |
| *B01J 8/18* | (2006.01) | |
| *B01J 8/00* | (2006.01) | |
| *B01J 8/26* | (2006.01) | |
| *C07C 1/20* | (2006.01) | |
| *B01J 19/02* | (2006.01) | |

(52) U.S. Cl.
CPC .............. *B01J 8/1827* (2013.01); *B01J 8/0055* (2013.01); *B01J 8/26* (2013.01); *B01J 19/02* (2013.01); *C07C 1/20* (2013.01); *B01J 2208/0084* (2013.01); *B01J 2208/00176* (2013.01); *B01J 2219/0004* (2013.01); *B01J 2219/0218* (2013.01); *B01J 2219/0236* (2013.01); *C10G 2400/20* (2013.01)

(58) Field of Classification Search
USPC .......... 585/638, 639, 640, 641, 642; 422/241, 422/240, 198
See application file for complete search history.

(56) References Cited

U.S. PATENT DOCUMENTS

| | | | |
|---|---|---|---|
| 2003/0236441 A1 | 12/2003 | Clem et al. .................... | 585/639 |
| 2004/0077912 A1 | 4/2004 | Jones et al. ................... | 585/639 |
| 2007/0203383 A1 * | 8/2007 | Bozzano et al. .............. | 585/639 |
| 2009/0166259 A1 * | 7/2009 | Bradley et al. ................ | 422/241 |

FOREIGN PATENT DOCUMENTS

| | | | |
|---|---|---|---|
| DE | 3510608 A1 * | 10/1986 | |
| EP | 1895025 | 12/1998 | .............. C30B 11/00 |
| WO | WO9955649 | 11/1999 | .............. C07C 11/02 |
| WO | WO2004000765 | 12/2003 | ................ C07C 1/20 |
| WO | WO2007135052 | 11/2007 | .............. C07C 11/06 |

* cited by examiner

*Primary Examiner* — In Suk Bullock
*Assistant Examiner* — Sharon Pregler (57) ABSTRACT

A process and a reactor system for the preparation of an olefinic product by reacting an oxygenate feedstock in the presence of an oxygenate conversion catalyst within a reactor system under oxygenate-to-olefin conversion conditions, to obtain the olefinic product, wherein the reactor system has a contact surface coming in contact with oxygenates and wherein at least part of the contact surface is an material of the formula MX wherein: M is a metal and X is C, or M is a metal or Si and X is N.

10 Claims, 2 Drawing Sheets

Fig.1

PROCESS AND REACTOR SYSTEM FOR THE PREPARATION OF AN OLEFINIC PRODUCT

PRIORITY CLAIM

The present application claims priority from PCT/EP2009/067625, filed 22 Dec. 2009, which claims priority from European Application 08172550.9, filed 22 Dec. 2008.

BACKGROUND

This invention relates to a process and a reactor system for the preparation of an olefinic product, in particular including lower olefins such as ethylene and/or propylene. More in particular this invention relates to a process for the conversion of oxygenates into olefins.

Processes for the preparation of olefins from oxygenates are known in the art. Of particular interest is often the production of light olefins, in particular ethylene and/or propylene. The oxygenate feedstock can for example comprise methanol and/or dimethylether, and an interesting route includes their production from synthesis gas derived from e.g. natural gas or via coal gasification.

For example, WO2007/135052 discloses a process wherein an alcohol and/or ether containing oxygenate feedstock and an olefinic co-feed are reacted in the presence of a zeolite having one-dimensional 10-membered ring channels to prepare an olefinic reaction mixture, and wherein part of the obtained olefinic reaction mixture is recycled as olefinic co-feed. With a methanol and/or dimethylether containing feedstock, and an olefinic co-feed comprising C4 and/or C5 olefins, an olefinic product rich in light olefins can be obtained.

International patent application with publication No. WO 2004/000765 discloses another oxygenate-to-olefin conversion process, an oxygenated feedstock, most preferably a methanol containing feedstock, is converted in the presence of a molecular sieve catalyst composition into one or more olefin(s), preferably and predominantly, ethylene and/or propylene, often referred to as light olefin(s). It is therein recognized as a problem, that metals in conventional reactor walls may act as catalysts in one or more side reactions, so that undesirable by-products are formed. For example, methanol can be catalytically converted into hydrogen, carbon monoxide, carbon dioxide, methane and/or graphite. By-products are undesirable for various reasons. Their formation lowers the yield of desired products, increased measures are needed for their separation and handling, and they can cause fouling in the reactor system.

According to WO 2004/000765, the inner surface of the feed introduction nozzle of the reactor system is maintained at a temperature below 400 C, most preferred embodiments are below 150° C. It was found that in a reactor operated below this temperature only negligible amounts methanol are converted. The control experiments disclosed therein included a reactor with a silica coating.

The low temperature of the inlet nozzle in WO 2004/000765 can be achieved by a low temperature of the feedstock, or providing a cooling system or thermal insulation for the nozzle. However a cooling system for the nozzle adds to the complexity of the reactor system, and durable thermal insulation faces practical difficulties when the mechanical duty is high, such as at the inlet of a riser reactor to which catalyst particles are fed as well as fluid reactants. Moreover reaction temperatures are sufficient to cause some decomposition of methanol.

In US2004/0077912, the nozzle is coated with a material resistant to the formation of metal-catalyzed side reaction byproducts, in particularly metal alloys and more in particular stainless steel are preferred, althoughsome non-metal materials are also mentioned. In the example, a stainless steel reactor was used, and a silica coated reactor was used for a control experiment. For the stainless steel, temperature control is still necessary, as explained in paragraph 86 and table 2, where the 316stainless steel reactor converts a significant amount of methanol above 450° C.

Oxygenate-to-olefin processes often operate at temperatures exceeding 400 C, 450 C, or even 500 C, and the metal-catalysed production of by-products increases with temperature. It is not generally sufficient to only deal with the methanol decomposition at the inlet nozzle to a reactor system. Also parts within the reactor system are exposed to oxygenates. Building a large part of a reactor system from stainless steel is uneconomic. A particular problem is encountered in fast-fluidized bed or riser reactor systems, where the catalyst particles are moving at high velocities, so that abrasion resistance is of importance. Stainless steel has lower hardness than carbon steel. Likewise, a silica coating would be insufficiently abrasion-resistant.

SUMMARY OF THE INVENTION

There is a need for an improved way of lowering the formation of by-products in oxygenate-to olefin conversion processes caused by catalytic activity of the metal in the reactor system, in particular allowing use under highly abrasive conditions. In accordance with the invention there is provided a process for the preparation of an olefinic product by reacting an oxygenate feedstock in the presence of an oxygenate conversion catalyst within a reactor system under oxygenate-to-olefin conversion conditions, to obtain the olefinic product, wherein the reactor system has a contact surface coming in contact with oxygenates and wherein at least part of the contact surface is an material of the formula MX wherein:
M is a metal and X is C, or
M is a metal or Si and X is N.

DETAILED DESCRIPTION OF THE INVENTION

Applicant has realized that this class of materials provides excellent suppression of methanol decomposition, together with other advantageous properties that are of importance in the practical design and operation of a reactor system. On the one hand these materials can advantageously be provided as coatings on e.g. carbon steel, not requiring an extensive use of stainless steel parts. A material of the formula MX, wherein M is a metal, and X is one of N and C, will in the following also referred to as an inert material.

It is noted that the silica coating used for comparative examples in WO 2004/000765 is clearly not a useful option to be used in a practical reactor system. Not only does silica have a low hardness, which can for example be expressed as a microhardness of well below 610 kg·mm$^{-2}$, see K. Aikawa et al, Journal of Materials Science vol. 13 (1987) p. 37-42. Also it is known that silica is subject to hydrothermal degradation which makes it unsuitable in an oxygenate-to olefins reactor system, where such conditions prevail.

The materials of the invention exhibit high abrasion resistance, so that they are very suitable for use in any part of a riser reactor system.

In a preferred embodiment, the microhardness, in particular the Vickers hardness, of the contact surface is 2000 kg·mm$^{-2}$ or higher. It was found that at a lower microhardness abrasion-resistance is insufficient, in particular in a fast-fluidized bed or riser reactor environment.

The microhardness of a material can be determined by standard tests according to ASTM E-384.

For example, the microhardness of TiN is above 2000 kg·mm$^{-2}$. The company BryCoat specifies 2500-3000 kg·mm$^{-2}$.

The microhardness of CrN is specified by the company BryCoat as 2200 kg·mm$^{-2}$.

The microhardness of SiC is specified by the company Accuratus as 2800 kg·mm$^{-2}$.

In a preferred embodiment, it has been found that titanium nitride effectively suppresses catalytic activity of the contact surface in oxygenate-to-olefin conversion. The reaction can be operated at a higher temperature of the contact surface without undue methanol decomposition.

Preferably the inert material is a layer on a substrate, e.g. a coating. Alternatively the whole article may be made from the inert material.

The thickness of the layer may be in the range of from 0.1 to 50 microns, preferably from 0.5 to 10 microns, such as from 1 to 5 microns.

The inert material may have a thermal conductivity of more than 4 J/sec·m·K.

The metal M may be selected from the group consisting of Cr, Ti, B and Zr; preferably from Ti and Zr, especially Ti. For preferred embodiments MX is one of ZrN and TiN.

Typically the temperature of the contact surface with the inert material can exceed 350° C., in particular can exceed 400° C., more in particular can exceed 450° C. Normally the temperature of the contact surface with the inert material is less than 650° C., especially less than 600° C., often less than 550° C.

The oxygenate feedstock comprises oxygenate species having an oxygen-bonded methyl group, such as methanol, dimethylether. Preferably the oxygenate feedstock comprises at least 50 wt % of methanol and/or dimethylether, more preferably at least 80 wt %, even more preferably at least 90 wt %. The oxygenate feedstock can comprise an amount of water, preferably less than 10 wt %, more preferably less than 5 wt %. Preferably the oxygenate feedstock contains essentially no hydrocarbons other than oxygenates, i.e. less than 5 wt %, preferably less than 1 wt %.

In one embodiment, the oxygenate is obtained as a reaction product of synthesis gas. Synthesis gas can for example be generated from fossil fuels, such as from natural gas or oil, or from the gasification of coal. Suitable processes for this purpose are for example discussed in Industrial Organic Chemistry, Klaus Weissermehl and Hans-Jürgen Arpe, 3rd edition, Wiley, 1997, pages 13-28. This book also describes the manufacture of methanol from synthesis gas on pages 28-30.

In another embodiment the oxygenate is obtained from biomaterials, such as through fermentation. For example by a process as described in DE-A-10043644.

Thus the oxygenates can be a feedstock, such as methanol, or reaction products/intermediates, such as dimethyl ether.

The oxygenate feedstock can be obtained from a prereactor, which converts methanol at least partially into dimethylether and water. Water may be removed by e.g. distillation. In this way, less water is present in the process of converting oxygenate to olefins, which has advantages for the process design and lowers the severity of hydrothermal conditions the catalyst is exposed to.

Thus the reactor system may comprise at least one of, preferably any two of, especially all of: a pre-rector for converting at least some methanol to dimethylether, a heater for heating the oxygenates and a main reactor for converting oxygenates to olefins.

Optionally said contact surface of the reactor system coming into contact with oxygenates, comprises a contact surface of said heater.

Preferably the oxygenate feed into the main reactor is at a temperature of above 300° C. preferably above 350° C.

Normally the main reactor has an inlet for oxygenate feedstock, such as a nozzle. Optionally said contact surface of the reactor system coming into contact with oxygenates, comprises a contact surface of said inlet.

The temperature of the nozzle can be above 400° C., in particular above 450° C.

Preferably the oxygenate feedstock is reacted to produce the olefinic product in the presence of an olefinic co-feed. By an olefinic composition or stream, such as an olefinic product, product fraction, fraction, effluent, reaction effluent or the like is understood a composition or stream comprising one or more olefins, unless specifically indicated otherwise. Other species can be present as well. Apart from olefins, the olefinic co-feed may contain other hydrocarbon compounds, such as for example paraffinic compounds. Preferably the olefinic co-feed comprises an olefinic portion of more than 50 wt %, more preferably more than 60 wt %, still more preferably more than 70 wt %, which olefinic portion consists of olefin(s). The olefinic co-feed can also consist essentially of olefin(s).

Any non-olefinic compounds in the olefinic co-feed are preferably paraffinic compounds. Such paraffinic compounds are preferably present in an amount in the range from 0 to 50 wt %, more preferably in the range from 0 to 40 wt %, still more preferably in the range from 0 to 30 wt %.

By an olefin is understood an organic compound containing at least two carbon atoms connected by a double bond. The olefin can be a mono-olefin, having one double bond, or a poly-olefin, having two or more double bonds. Preferably olefins present in the olefinic co-feed are mono-olefins. C4 olefins, also referred to as butenes (1-butene, 2-butene, iso-butene, and/or butadiene), in particular C4 mono-olefins, are preferred components in the olefinic co-feed.

Preferably the olefinic co-feed is at least partially obtained by a recycle stream formed by recycling a suitable fraction of the reaction product comprising C4 olefin. The skilled artisan knows how to obtain such a fractions from the olefinic reaction effluent such as by distillation.

In one embodiment at least 70 wt % of the olefinic co-feed, during normal operation, is formed by the recycle stream, preferably at least 90 wt %, more preferably at least 99 wt %. Most preferably the olefinic co-feed is during normal operation formed by the recycle stream, so that the process converts oxygenate feedstock to predominantly light olefins without the need for an external olefins stream. During normal operation means for example in the course of a continuous operation of the process, for at least 70% of the time on stream. The olefinic co-feed may need to be obtained from an external source, such as from a catalytic cracking unit or from a naphtha cracker, during start-up of the process, when the reaction effluent comprises no or insufficient C4+ olefins.

A particularly preferred olefinic recycle stream is a C4 fraction containing C4 olefin(s), but which can also contain a significant amount of other C4 hydrocarbon species, in particular C4 paraffins, because it is difficult to economically separate C4 olefins and paraffins, such as by distillation.

In a preferred embodiment the olefinic co-feed and preferably also the recycle stream comprises C4 olefins and less than 10 wt % of C5+ hydrocarbon species, more preferably at least 50 wt % of C4 olefins, and at least a total of 70 wt % of C4 hydrocarbon species.

The olefinic co-feed and preferably also the recycle stream, can in particular contain at least a total of 90 wt % of C4 hydrocarbon species. In a preferred embodiment, the olefinic co-feed comprises less than 5 wt % of C5+ olefins, preferably less than 2 wt % of C5+ olefins, even more preferably less than 1 wt % of C5+ olefins, and likewise the recycle stream. In another preferred embodiment, the olefinic co-feed, comprises less than 5 wt % of C5+ hydrocarbon species, preferably less than 2 wt % of C5+ hydrocarbon species even more preferably less than 1 wt % of C5+ hydrocarbon species, and likewise the recycle stream.

Thus in certain preferred embodiments, the olefinic portion of the olefinic co-feed, and of the recycle stream, comprises at least 90 wt % of C4 olefins, more preferably at least 99 wt %. Butenes as co-feed have been found to be particularly beneficial for high ethylene selectivity. Therefore one particularly suitable recycle stream consists essentially, i.e. for at least 99 wt %, of 1-butene, 2-butene (cis and trans), isobutene, n-butane, isobutene, butadiene.

In certain embodiments, the recycle stream can also comprise propylene. This may be preferred when a particularly high production of ethylene is desired, so that part or all of the propylene produced, such as at least 5 wt % thereof, is recycled together with C4 olefins.

The preferred molar ratio of oxygenate in the oxygenate feedstock to olefin in the olefinic co-feed depends on the specific oxygenate used and the number of reactive oxygen-bonded alkyl groups therein. Preferably the molar ratio of oxygenate to olefin in the total feed lies in the range of 10:1 to 1:10, more preferably in the range of 5:1 to 1:5 and still more preferably in the range of 3:1 to 1:3.

In a preferred embodiment wherein the oxygenate comprises only one oxygen-bonded methyl group, such as methanol, the molar ratio preferably lies in the range from 5:1 to 1:5 and more preferably in the range of 2.5:1 to 1:2.5.

In another preferred embodiment wherein the oxygenate comprises two oxygen-bonded methyl groups, such as for example dimethylether, the molar ratio preferably lies in the range from 5:2 to 1:10 and more preferably in the range of 2:1 to 1:4. Most preferably the molar ratio in such a case is in the range of 1.5:1 to 1:3.

The process to prepare an olefin is preferably carried out in presence of a molecular sieve having one-dimensional 10-membered ring channels. These are understood to be molecular sieves having only 10-membered ring channels in one direction which are not intersected by other 8, 10 or 12-membered ring channels from another direction.

Preferably, the molecular sieve is selected from the group of TON-type (for example zeolite ZSM-22), MTT-type (for example zeolite ZSM-23), STF-type (for example SSZ-35), SFF-type (for example SSZ-44), EUO-type (for example ZSM-50), and EU-2-type molecular sieves or mixtures thereof.

MTT-type catalysts are more particularly described in e.g. U.S. Pat. No. 4,076,842. For purposes of the present invention, MTT is considered to include its isotypes, e.g., ZSM-23, EU-13, ISI-4 and KZ-1.

TON-type molecular sieves are more particularly described in e.g. U.S. Pat. No. 4,556,477. For purposes of the present invention, TON is considered to include its isotypes, e.g., ZSM-22, Theta-1, ISI-1, KZ-2 and NU-10.

EU-2-type molecular sieves are more particularly described in e.g. U.S. Pat. No. 4,397,827. For purposes of the present invention, EU-2 is considered to include its isotypes, e.g., ZSM-48.

In a further preferred embodiment a molecular sieve of the MTT-type, such as ZSM-23, and/or a TON-type, such as ZSM-22 is used.

The molecular sieve can in particular be an aluminosilicate. An aluminosilicate molecular sieve is also referred to as a zeolite. Molecular sieve and zeolite types are for example defined in Ch. Baerlocher and L. B. McCusker, Database of Zeolite Structures: http://www.iza-structure.org/databases/, which database was designed and implemented on behalf of the Structure Commission of the International Zeolite Association (IZA-SC), and based on the data of the 4th edition of the Atlas of Zeolite Structure Types (W. M. Meier, D. H. Olson and Ch. Baerlocher).

Preferably, molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. When the molecular sieves are prepared in the presence of organic cations the molecular sieve may be activated by heating in an inert or oxidative atmosphere to remove organic cations, for example, by heating at a temperature over 500° C. for 1 hour or more. The zeolite is typically obtained in the sodium or potassium form. The hydrogen form can then be obtained by an ion exchange procedure with ammonium salts followed by another heat treatment, for example in an inert or oxidative atmosphere at a temperature over 300° C. The molecular sieves obtained after ion-exchange are also referred to as being in the ammonium form.

In a preferred embodiment the molecular sieve having one-dimensional 10-membered ring channels comprises at least one of a molecular sieve of the MTT-type and/or of the TON-type. Examples are ZSM-23 for MTT, and ZSM-22 for TON.

Preferably the molecular sieve having one-dimensional 10-membered ring channels has a silica-to-alumina ratio (SAR) in the range from 1 to 500, preferably in the range from 10 to 200. The SAR is defined as the molar ratio of $SiO_2/Al_2O_3$ corresponding to the composition of the molecular sieve.

For ZSM-22, a SAR in the range of 40-150 is preferred, in particular in the range of 70-120. Good performance in terms of activity and selectivity has been observed with a SAR of about 100.

For ZSM-23, an SAR in the range of preferably the SAR is in the range of 2-120, more preferably 10-100, especially 30-80. Good performance in terms of activity and selectivity has been observed with a SAR of about 50.

In a special embodiment the reaction is performed in the presence of a more-dimensional molecular sieve, such as ZSM-5. Suitably to this end the oxygenate conversion catalyst comprises at least 1 wt %, based on total molecular sieve in the oxygenate conversion catalyst, of a further molecular sieve having more-dimensional channels, in particular at least 5 wt %, more in particular at least 8 wt %.

The further molecular sieve having more-dimensional channels is understood to have intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. The second molecular sieve can be for example a FER type zeolite which is a two-dimensional structure and has 8- and 10-membered rings intersecting each other. Preferably however the intersecting channels in the second molecular sieve are each 10-membered ring channels. Thus the second molecular sieve may be a zeolite, or a SAPO-type (silicoaluminophosphate) molecular sieve. More preferably however the second molecular sieve is a zeolite. A preferred second molecular sieve is an MFI-type zeolite, in particular zeolite ZSM-5.

The presence of the further molecular sieve in the oxygenate conversion catalyst was found to improve stability (slower deactivation during extended runs) and hydrothermal stability compared to a catalyst with only the one-dimensional molecular sieve and without the more-dimensional molecular sieve. Without wishing to be bound by a particular hypothesis or theory, it is presently believed that this is due to the possibility for converting larger molecules by the second molecular sieve having more-dimensional channels, that were produced by the first molecular sieve having one-dimensional 10-membered ring channels, and which would otherwise form coke. When the one-dimensional aluminosiclicate and the more-dimensional molecular sieve are formulated such that they are present in the same catalyst particle, such as in a spray-dried particle, this intimate mix was found to improve the selectivity towards ethylene and propylene, more in particular towards ethylene. The weight ratio between the molecular sieve having one-dimensional 10-membered ring channels, and the further molecular sieve having more-dimensional channels can be in the range of from 1:100 to 100:1. Preferably the further molecular sieve is the minority component, i.e. the above weight ratio is 1:1 to 100:1, more preferably in the range of 9:1 to 2:1.

Preferably the further molecular sieve is a MFI-type molecular sieve, in particular zeolite ZSM-5, having a Silica-to-Alumina ratio SAR of at least 60, more preferably at least 80, even more preferably at least 100, yet more preferably at least 150. At higher SAR the percentage of C4 saturates in the C4 totals produced is minimized. In special embodiments the oxygenate conversion catalyst can comprise less than 35 wt % of the further molecular sieve, based on the total molecular sieve in the oxygenate conversion catalyst, in particular less than 20 wt %, more in particular less than 18 wt %, still more in particular less than 15 wt %.

In one embodiment the oxygenate conversion catalyst can comprise more than 50 wt %, at least 65 wt %, based on total molecular sieve in the oxygenate conversion catalyst, of the molecular sieve having one-dimensional 10-membered ring channels. The presence of a majority of such molecular sieve strongly determines the predominant reaction pathway.

The molecular sieve can be used as such or in a formulation, such as in a mixture or combination with a so-called binder material and/or a filler material, and optionally also with an active matrix component. Other components can also be present in the formulation. If one or more molecular sieves are used as such, in particular when no binder, filler, or active matrix material is used, the molecular sieve itself is/are referred to as oxygenate conversion catalyst. In a formulation, the molecular sieve in combination with the other components of the mixture such as binder and/or filler material is/are referred to as oxygenate conversion catalyst.

It is desirable to provide a catalyst having good mechanical or crush strength, because in an industrial environment the catalyst is often subjected to rough handling, which tends to break down the catalyst into powder-like material. The latter causes problems in the processing. Preferably the molecular sieve is therefore incorporated in a binder material. Examples of suitable materials in a formulation include active and inactive materials and synthetic or naturally occurring zeolites as well as inorganic materials such as clays, silica, alumina, silica-alumina, titania, zirconia and aluminosilicate. For present purposes, inert materials, such as silica, are preferred because they may prevent unwanted side reactions which may take place in case a more acidic material, such as alumina or silica-alumina is used.

The process of the present invention can be carried out in a batch, continuous, semi-batch or semi-continuous manner. Preferably the process of the present invention is carried out in a continuous manner.

If the process is carried out in a continuous manner, the process may be started up by using olefins obtained from an external source for the olefinic co-feed, if used. Such olefins may for example be obtained from a steam cracker, a catalytic cracker, alkane dehydrogenation (e.g. propane or butane dehydrogenation). Further, such olefins can be bought from the market.

In a special embodiment the olefins for such start-up are obtained from a previous process that converted oxygenates, with or without olefinic co-feed, to olefins. Such a previous process may have been located at a different location or it may have been carried out at an earlier point in time.

When a molecular sieve having more-dimensional channels such as ZSM-5 is present in the oxygenate conversion catalyst, even in minority compared to the molecular sieve having one-dimensional 10-membered ring channels, start up is possible without an olefinic co-feed from an external source. ZSM-5 for example is able to convert an oxygenate to an olefin-containing product, so that a recycle can be established.

Typically the oxygenate conversion catalyst deactivates in the course of the process. Conventional catalyst regeneration techniques can be employed, such as burning of coke in a regenerator. The molecular sieve having one-dimensional 10-membered ring channels used in the process of the present invention can have any shape known to the skilled person to be suitable for this purpose, for it can be present in the form of spray-dried particles, spheres, tablets, rings, extrudates, etc. Extruded catalysts can be applied in various shapes, such as, cylinders and trilobes. If desired, spent oxygenate conversion catalyst can be regenerated and recycled to the process of the invention.

The reaction to produce the olefins can be carried out over a wide range of temperatures and pressures. Suitably, however, the oxygenate feed and olefinic co-feed are contacted with the molecular sieve at a temperature in the range from 200° C. to 650° C. In a further preferred embodiment the temperature is in the range from 250° C. to 600° C., more preferably in the range from 300° C. to 550° C., most preferably in the range from 450° C. to 550° C. Preferably the reaction to produce the olefins is conducted at a temperature of more than 450° C., preferably at a temperature of 460° C. or higher, more preferably at a temperature of 490° C. or higher. At higher temperatures a higher activity and ethylene selectivity is observed. Molecular sieves having one-dimensional 10-membered ring channels can be operated under oxygenate conversion conditions at such high temperatures with acceptable deactivation due to coking, contrary to molecular sieves with smaller pores or channels, such as 8-membered ring channels. Temperatures referred to hereinabove represent reaction temperatures, and it will be understood that a reaction temperature can be an average of temperatures of various feed streams and the catalyst in the reaction zone.

In addition to the oxygenate, and the olefinic co-feed, a diluent may be fed into the reactor system. It is preferred to operate without a diluent, or with a minimum amount of diluent, such as less than 200 wt % of diluent based on the total amount of oxygenate feed, in particular less than 100 wt %, more in particular less than 20 wt %. Any diluent known by the skilled person to be suitable for such purpose can be used. Such diluent can for example be a paraffinic compound or mixture of compounds. Preferably, however, the diluent is an inert gas. The diluent can be argon, nitrogen, and/or steam. Of these, steam is the most preferred diluent. For example, the oxygenate feed and optionally olefinic co-feed can be diluted with steam, for example in the range from 0.01 to 10 kg steam per kg oxygenate feed.

In one embodiment small amounts of water are added in order to improve the stability of the catalyst by reducing coke formation.

The olefinic product or reaction effluent is typically fractionated. The skilled artisan knows how to separate a mixture of hydrocarbons into various fractions, and how to work up fractions further for desired properties and composition for further use. The separations can be carried out by any method known to the skilled person in the art to be suitable for this purpose, for example by vapour-liquid separation (e.g. flashing), distillation, extraction, membrane separation or a combination of such methods. Preferably the separations are carried out by means of distillation. It is within the skill of the artisan to determine the correct conditions in a fractionation column to arrive at such a separation. He may choose the correct conditions based on, inter alia, fractionation temperature, pressure, trays, reflux and reboiler ratios.

In one embodiment, a light olefinic fraction comprising ethylene and a heavier olefinic fraction comprising C4 olefins and less than 10 wt % of C5+ hydrocarbon species can be obtained. Preferably also a water-rich fraction is obtained. Also a lighter fraction comprising methane, carbon monoxide, and/or carbon dioxide can be obtained, as well as one or more heavy fractions comprising C5+ hydrocarbons. Such heavy fraction can for example be used as gasoline blending component.

In the process also a significant amount of propylene is normally produced. The propylene can form part of the light olefinic fraction comprising ethene, and which can suitably be further fractionated into various product components. Propylene can also form part of the heavier olefinic fraction comprising C4 olefins. The various fractions an streams referred to herein, in particular the recycle stream, can be obtained by fractionating in various stages, and also by blending streams obtained during the fractionation. Typically, an ethylene and a propylene stream of predetermined purity such as pipeline grade, polymer grade, chemical grade or export quality will be obtained from the process, and also a stream rich in C4 comprising C4 olefins and optionally C4 paraffins. It shall be clear that the heavier olefinic fraction comprising C4 olefins, forming the recycle stream in step c), can be composed from quantities of various fractionation streams. So, for example, some amount of a propylene-rich stream can be blended into a C4 olefin-rich stream. In a particular embodiment at least 90 wt % of the heavier olefinic fraction comprising C4 olefins can be formed by the overhead stream from a debutaniser column receiving the bottom stream from a depropanizer column at their inlet, more in particular at least 99 wt % or substantially all.

Suitably the olefinic reaction effluent comprises less than 10 wt %, preferably less than 5 wt %, more preferably less than 1 wt %, of C6-C8 aromatics. Producing low amounts of aromatics is desired since any production of aromatics consumes oxygenate which is therefore not converted to lower olefins.

The invention also provides a reactor system suitable for the preparation of an olefinic product by reacting an oxygenate feedstock in the presence of an oxygenate conversion catalyst under oxygenate-to-olefin conversion conditions, to obtain the olefinic product, wherein the reactor system has a contact surface coming in contact with oxygenate feedstock and/or reaction products, and wherein at least part of the contact surface is an inert material of the formula MX wherein: M is a metal and X is one of N and C. Typically said surface of the reactor system coming in contact with oxygenate feedstock and/or reaction products comprises at least one selected from the group consisting of: a heater for oxygenate feedstock, an inlet for oxygenate feedstock, a reactor wall and reactor internals (in particular riser reactor internals) such as wall anchors, weirs, flow distributors, contacting devices (e.g. those known from EP 931 121 B1), standpipes and cyclones; especially an inlet for oxygenate feedstock.

The reactor system may be any reactor known to the skilled person and may for example contain a fixed bed, moving bed, fluidized bed, riser reactor and the like. A riser reactor system is preferred, in particular a riser reactor system comprising a plurality of serially arranged riser reactor stages.

Figure 1:
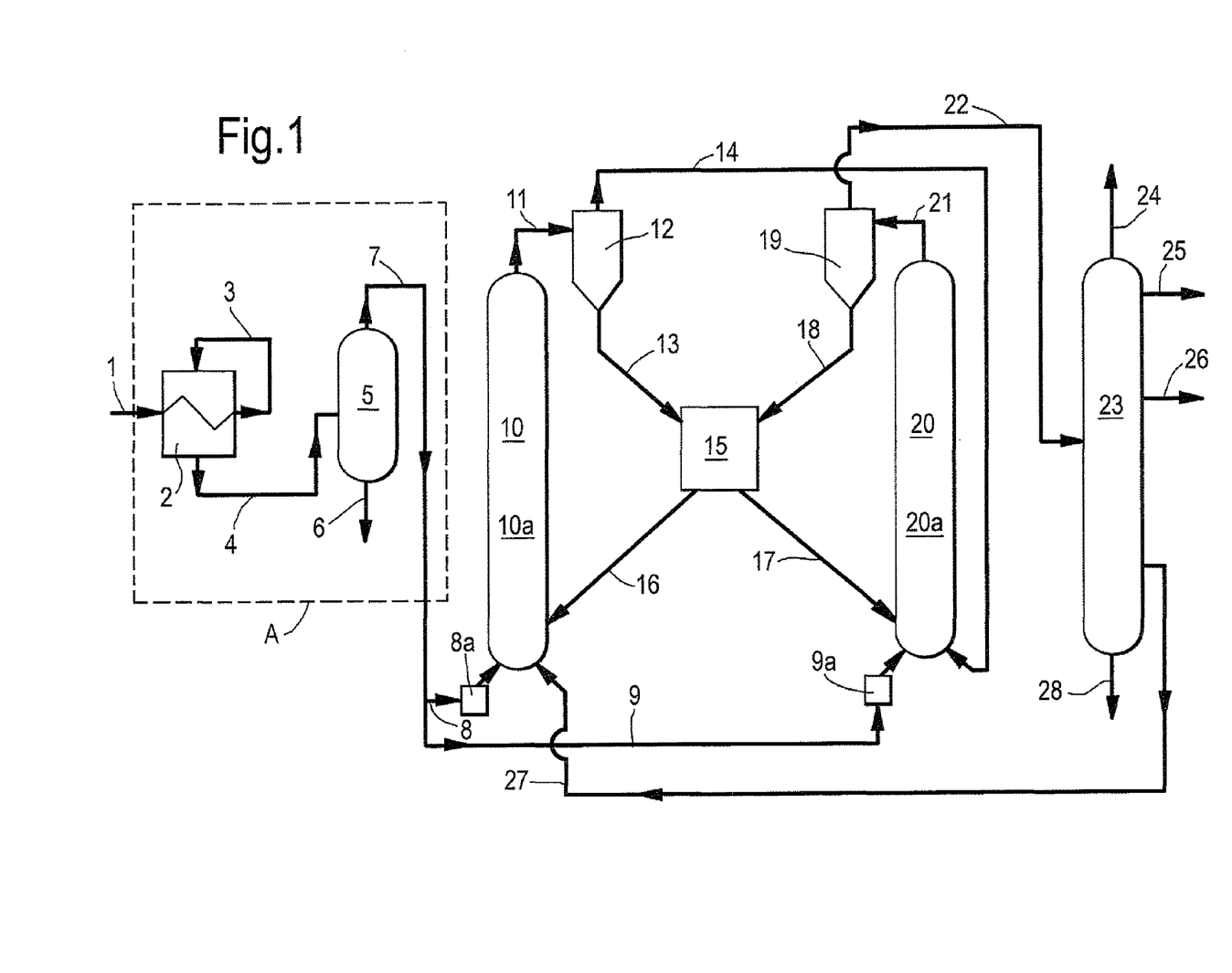
FIG. 1 schematically shows a reactor-system in accordance with the invention.
Figure 2:
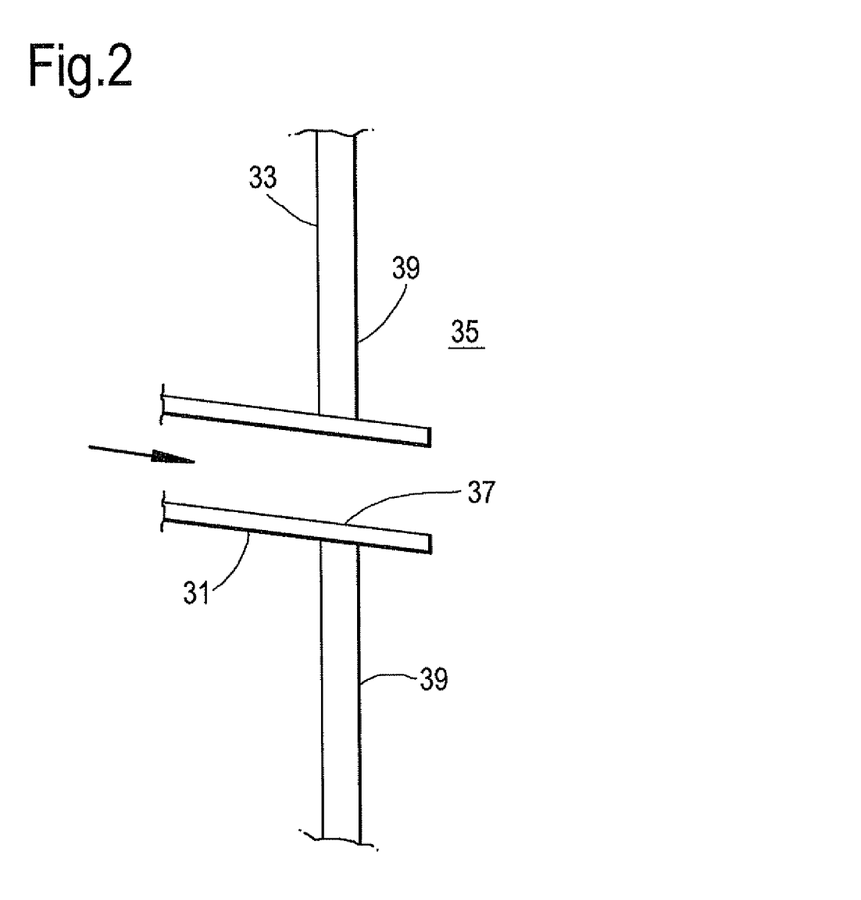
FIG. 2 shows schematically an inlet nozzle into a riser reactor in accordance with the invention.

The process of the present invention will be elucidated by way of example, with reference to the accompanying Figures, wherein FIG. 1 schematically shows a reactor-system in accordance with the invention;

FIG. 2 shows schematically an inlet nozzle into a riser reactor in accordance with the invention.

In the embodiment of FIG. 1, alkyl alcohol, e.g. methanol, is first passed through a prereactor section A to convert alkyl alcohol into dialkylether, e.g. dimethylether. Vaporous alkyl alcohol is passed via a line 1 through coolant tubes in a dialkylether reactor 2. As the formation of dialkylether from alkyl alcohol is exothermic, the vaporous alkyl alcohol is heated and the thus heated alkyl alcohol leaves the reactor as hot effluent via a line 3. The hot effluent is subsequently recycled to the reactor 2 but at the reaction side of the coolant tubes. The stream from line 1 and the one from line 3 are passed co-currently through reactor 2. In reactor 2 the alkyl alcohol is converted to dialkylether and water in contact with a suitable catalyst, e.g. gamma-alumina. A dialkylether product stream comprising dialkylether, water and alkyl alcohol leaves the reactor via a line 4. The hot dialkylether product stream may be cooled before being passed on to a separation section 5. The stream may be cooled in one or more stages, e.g., by indirect heat exchange and/or by flashing in a flash vessel wherein the pressure is reduced and the product stream is cooled (not shown). In the separation section 5, here depicted as a fractionation column, the dialkylether product stream is separated into a liquid stream 6 comprising water and preferably less than 1% wt alkyl alcohol, based on the total of water and alkyl alcohol, and a vaporous dialkylether-rich stream 7, comprising dialkylether, the majority of the alkyl alcohol and typically some water, such as more than 0.5 wt %, in particular more than 1 wt %, and less than 10 wt % or preferably less than 5 wt %, based on the total dialkylether-rich stream.

The stream in line 7 may be split into several portions. In the case of the embodiment depicted in the present figure there are two portions, but it will be evident that when more portions are desired in view of the number of reactors the number can be adapted. The portion in line 8 is heated to a desired inlet temperature in preheater 8a, and fed to a first riser reactor 10 of a serial riser reactor system, typically via an inlet nozzle. This will be further discussed with reference to FIG. 2. The portion in line 9 is fed, via a preheater 9a, to a second riser reactor 20 of the serial riser reactor system. Depending on the temperature of the stream in line 7 and the desired inlet temperatures of the oxygenate feed to the first and second riser reactors, one or both of the preheaters can be omitted, or instead a heat exchanger or coolers can be arranged in their place. It is also possible to arrange more oxygenate inlet nozzles further up in a riser reactor for oxygenate feed staging.

A stream of an olefinic co-feed, comprising e.g. olefins with 4 and/or 5 carbon atoms which stream is provided via a line 27 to the inlet end of the first riser reactor 10. The stream can be combined with the stream 8 before entering the reactor.

In the riser reactor 10 the streams from lines 8 and 27 are contacted with a suitable catalyst, provided via a standpipe 16, and the formed combination of oxygenate (i.e. dialkylether and alkyl alcohol), olefin, water and catalyst is passed upwards and this combination leaves the riser reactor 10 via a line 11 as reaction product. The riser reactors can be provided with reactor internals, e.g. contacting devices, generally denoted with reference numerals 10a, 20a.

Via line 11 the reaction product is passed to a separation means, e.g. a cyclone 12, from which catalyst particles are discharged via a line 13 and passed to a catalyst buffer vessel 15, and from which the vaporous reaction product, comprising dialkylether, olefins and water is withdrawn via line 14. This vaporous product in line 14 is, together with the portion of the dialkylether-rich feed in line 9, passed to the second riser reactor 20, in which a similar reaction takes place as in riser reactor 10. Lines 14 and 9 may also be combined before entering the riser reactor 20. Catalyst for riser reactor 20 is provided via line 17. The reaction product of the riser reactor 20 is discharged therefrom via line 21 and passed to a separation means 19, e.g. a cyclone. In the separation means catalyst particles are separated from the vaporous products and withdrawn from the separation means 19 via a line 18 and passed to the catalyst buffer vessel 15.

It will be realised that at the dialkylether conversion reaction some coke formation may take place, which coke may deposit on the catalyst particles.

Therefore, it is advantageous to regenerate the catalyst particles periodically. Conveniently this may be achieved by continuously or periodically withdrawing part of the catalyst inventory of the catalyst buffer vessel 15 and passing it to a regeneration vessel (not shown), where typically coke is burned partially or substantially fully at temperatures of about 600° C. or more. The size of the portion sent to the regeneration vessel depends on the average degree of deactivation or coking, and on the regeneration conditions, e.g. partial or full burning of coke. The regenerated catalyst particles are recycled to the catalyst buffer vessel or to the riser reactor(s) directly. The regeneration is not shown in the figure.

As product from the separation means 19 an olefins-containing product stream is obtained in a line 22. This product is passed to a fractionation section, in the figure represented by a column 23 in which the olefins-containing product stream is separated into a light fraction 24, comprising light contaminants, such as carbon monoxide, carbon dioxide and methane, into an ethylene fraction 25, into a propylene fraction 26 and into a $C_4$ olefin fraction 27. Optionally, one or more heavier fractions, e.g. fractions with hydrocarbons with 5, 6 or 7+ hydrocarbons may be withdrawn separately from the column 23 (not shown). The separation section also includes a line 28 for withdrawing water. The light fraction in line 24 is discharged, e.g., combusted as fuel. Ethylene and propylene are recovered as products. Water in fraction 28 is withdrawn, and the $C_4$ fraction is recycled via line 27 to the dialkylether-rich stream in line 8.

FIG. 1 shows two riser reactors. It will be evident to the skilled person that only one reactor or more than two, e.g., 3 or 4, riser reactors may be used. Such use will also get the benefits of the present invention.

In another embodiment a serial riser reactor system is used that comprises e.g., three riser reactors that are serially arranged. Each riser reactor has at its lower portion one or more inlets, including an inlet for oxygenate, and at its upper portion one or more outlets. The outlet of the first riser reactor is connected with an inlet of the second riser. Likewise, the outlet of the second riser reactor is connected with an inlet of the third riser reactor.

During normal operation of the serial reactor system, the vaporous dialkylether-rich feed, olefinic co-feed and catalyst are fed to the first riser reactor. Conversion in the first riser over the catalyst forms an olefinic first reactor effluent comprising a gaseous product comprising olefins, and catalyst. Substantially the entire reactor effluent is fed to the inlet of the second riser reactor, together with a portion of the vaporous dialkylether-rich feed and additional catalyst. Although it is possible to also feed an olefinic co-feed to the second riser reactor, this is not needed and not necessarily advantageous, since the effluent from the first riser reactor already contains olefins.

Since additional catalyst is added to the second and third riser reactor, the mass flow rate (mass per unit of time) of oxygenate conversion catalyst in the second riser is higher than in the previous riser reactor. It is generally desired that the weight hourly space velocity remains substantially constant, i.e. not deviating more than 50% from that of the previous riser reactor. Therefore it is advantageous to arrange that the cross-section of the second riser reactor is larger than that of the first riser reactor. For cylindrical riser reactors, the increase in cross-section can also be expressed as an increase in diameter.

When the weight hourly space velocity is substantially constant, the time to flow through the riser reactor is the same for riser reactors of the same height.

The cross section of the third riser reactor is again larger than that of the second riser. It can be preferred to design each riser reactor and the respective catalyst throughput such that substantially full conversion of oxygenate is achieved in the riser reactor, this can be most desirable for the last riser reactor so that substantially no oxygenate forms part of the effluent from the last riser reactor.

The outlet from the last riser reactor is connected to a collector and separation means. The separation means can also be integrated with last riser reactor. It can be a large collector vessel combined with a plurality of cyclone separators, which can be internally housed in the collector vessel. The separation means has an outlet for vapour and an outlet for catalyst. The vapour contains olefins and may be treated in the same way as the vaporous product in line 22 of the Figure. The catalyst is returned to the riser reactors, whereas part may be regenerated as discussed in relation to the Figure.

In yet another embodiment, only a single riser is employed, and the oxygenate feed may enter via one or more inlets at one or various heights.

Several components of the reactor systems discussed hereinbefore and with reference to FIG. 1 can have contact surfaces with oxygenate, that are of an inert material in accordance with the present invention. Such components can be present in the prereactor section A. Importantly, the heaters 8a, 9a can have contact surfaces that are at high temperatures, in particular when they are fired heaters there can be hot contact surfaces with the oxygenate. But also in case unfired heaters (such as heat exchangers) are employed, it can be beneficial to design contact surfaces therein in accordance with the invention. Examples of other components that can have a contact surface in accordance with the invention are: standpipes 16,17 with catalyst inlets into the riser reactors, separation means 12,19, riser internals such as contact devices 10a, 20a.

FIG. 2 shows schematically an example of an inlet nozzle 31 for oxygenate feed. The nozzle reaches through the riser reactor wall 33, some distance into the riser interior 35. The inner surface 37 of the nozzle 31, is of an inert material in accordance with the invention, e.g. coated with TiN. Also, part of the inner surface 39 of the reactor wall 33, surrounding the nozzle 31 can come in contact with a significant oxygenate concentration during operation, and therefore at least part or all of this inner surface can be of an inert material, too.

EXAMPLES

Embodiments of the invention will now be described, by way of example only.

A variety of experiments were conducted to convert methanol to di-methyl ether (DME) in a flow through reactor having beds with various compounds which may be used as coatings. The experiments aimed to determine which compound would minimise side reactions, in particular, minimise methanol steam reforming (producing CO and $H_2$).

Experimental

Materials were evaluated in a nanoflow reactor apparatus. Typically, 50 to 350 mg of material mixed with 350 mg of SiC and loaded into a 3.6 mm ID quartz reactor tube, depending on the required space velocity. A particle size fraction of 40-60 mesh (420-250 μm) was commonly used.

In the experiments a methanol feed (6.7 vol % in Argon) was used, at temperatures above 100° C., and a pressure of 1 bara. In a typical experiment the reactor was heated to the required reaction temperature under a flow of Argon, before passing the gas stream containing the desired reactants over the catalyst. The required gas composition was obtained either by feeding and mixing the appropriate amounts of gaseous feeds or, in the case of methanol, this was vaporized by passing argon through a thermostated saturator to yield the target feed concentration.

The various individual gas streams were mixed into a single feed stream that was fed to the reactor tubes and regulated using flow controllers.

Flows were typically set in the range of 50 ml/min set under ambient conditions. Gas analysis was performed using mass spectrometry (MS) and gas chromatography (GC). After an equilibration time of about 3 minutes at a certain reaction condition, a gas sample was injected on to the capillary GC column (Petrocol DH, 100 m, 0.25 mm ID, layer thickness 0.5 μm) using a pneumatic Valco injection valve for analysis of hydrocarbons.

The physical mixture was heated to 100° C. in Argon after which the gaseous feed was passed over the reactor. The reactor was heated to increasing temperatures, and at each temperature the product distribution was measured.

Gas analysis was done using a mass spectrometer from Thermo type VG Prima δB (Faraday cup detector). Calibrations were performed to calculate the concentration of the components in the product stream. Conversion of methanol is defined as the difference of the inlet and outlet methanol concentration and divided by the inlet concentration. The gas hourly space velocity (GHSV) was calculated by dividing the total gas flow (olefin+oxygenate+water+argon) by the catalyst amount (unit: $ml \cdot g^{-1} \cdot h^{-1}$).

The following materials were tested

Quartz (not According to the Invention)

The reactors used were made of quartz, which consists of silicon dioxide able to easily withstand temperatures up to 700 C. To check that these reactors are inert, blank experiments were performed with an empty quartz reactor under typical reaction conditions and feed.

Silicon Carbide (SiC) (not According to the Invention)

Silicon carbide (40-60 mesh) was used as such, as well as for diluting various other materials. SiC was used as diluent to prevent pressure drops and/or to prevent complete plugging of a bed that does otherwise not allow any gas to pass through. When SiC was present, the reactor contained 350 mg of SiC, possibly in addition to other materials.

Iron (not According to the Invention)

Iron powder (obtained from Merck chemicals) was tested in a mixture of 250 mg Fe with 350 mg SiC.

Titanium Nitride (TiN)

TiN was obtained from Sigma-Aldrich™. Particles were <10 micron. TiN was tested in a mixture of 250 mg TiN with 350 mg SiC.

A good indicator of methanol decomposition is the hydrogen ($H_2$) concentration in the gas leaving the reactor, as well as the evolution of carbon monoxide and carbon dioxide. Methanol not only decomposes at elevated temperatures into H2, CO, CO2, but also converts to dimethylether (DME) and water. It is known that the decomposition of methanol occurs easier than the decomposition of DME.

Table 1 shows, for various temperatures, the concentration of H2 in the product from reactors with various fillings. H2 is a good indicator for methanol decomposition. Table 1 also shows the DME concentration in the product.

TABLE 1

| | $H_2$ and DME (in vol %) in the product for various reactor fillings and temperatures | | | | | | | |
|---|---|---|---|---|---|---|---|---|
| T/ °C. | empty reactor | | SiC | | SiC/Fe | | SiC/TiN | |
| Mol % | $H_2$ | DME | $H_2$ | DME | $H_2$ | DME | $H_2$ | DME |
| 300 | <0.3 | <0.3 | <0.3 | <0.3 | <0.3 | <0.3 | <0.3 | <0.3 |
| 350 | <0.3 | <0.3 | <0.3 | <0.3 | 0.7 | <0.3 | <0.3 | 0.3 |
| 400 | <0.3 | <0.3 | <0.3 | 0.9 | 1.3 | <0.3 | <0.3 | 1.6 |
| 450 | <0.3 | <0.3 | 0.6 | 1.7 | 4.2 | <0.3 | 0.5 | 2.8 |
| 500 | <0.3 | 0.3 | 1.1 | 1.7 | 9.3 | 0.5 | 0.6 | 2.5 |
| 550 | 0.3 | 0.4 | 0.7 | 1.4 | 8.9 | 0.7 | 0.5 | 2.6 |

As expected, the empty reactor shows only minimum conversion. SiC shows minimum decomposition at 450 C, as seen from the H2 data, and which stays moderate at higher temperatures as well. A similar behaviour is seen from the mixture of TiN and SiC, so that TiN alone also does not give rise to any significant methanol decomposition. The slight decrease in the $H_2$ concentrations that is observed with respect to SiC alone can be explained by the fact that the methanol conversion to DME is somewhat higher in the presence of TiN, and together with the fact that DME decomposes less easy than methanol.

Next to these fillings with inert materials according to the invention, a reactor filling containing iron (comparative) was also tested. Clearly, the SiC/Fe filling shows much higher decomposition than any of the other materials, and already at lower temperatures.

The slightly smaller absolute values for $H_2$ and DME concentrations at the highest temperature can be explained by coking that was observed then. Still, the ratio of the $H_2$ concentration produced in the iron containing reactor and the $H_2$ concentration produced SiC/TiN containing reactors increases at 550 C compared to lower temperatures. So, the advantage of inert materials according to the invention further increases, and they can beneficially be applied for contact surfaces in an oxygenate-to-olefins reactor, e.g. as a coating.

What is claimed is:

1. A process for the preparation of an olefinic product comprising reacting an oxygenate feedstock in the presence of an oxygenate conversion catalyst within a reactor system under oxygenate-to-olefin conversion conditions, to obtain the olefinic product,
wherein the reactor system has a contact surface coming in contact with oxygenates and wherein at least part of the contact surface is an inert material of the formula MX wherein:
M is a metal or Si and X is C or N wherein said metal is selected from the group consisting of Ti, B, and Zr.

2. A process according to claim 1, wherein the inert material has the form of a layer of the inert material on a substrate.

3. A process according to claim 1, wherein the inert material has a microhardness of at least 2000 $kgmm^{-2}$.

4. A process according to claim 1, wherein MX is one of ZrN and TiN.

5. A process according to claim 1, wherein the temperature of the contact surface with an inert material that comes in contact with the oxygenate is at a temperature exceeding 350 C.

6. A process according to claim 1, wherein the reactor system comprises a heater for oxygenate feedstock and a contact surface of said heater comprises said inert material.

7. A process according to claim 1, wherein the reactor system comprises an inlet for oxygenate feedstock, and said contact surface of the reactor system coming into contact with oxygenates, comprises a contact surface of said inlet.

8. A process according to claim 1, wherein the reactor system comprises at least one component selected from the group of a reactor wall, a reactor internal, a standpipe and a cyclone and said contact surface of the reactor system coming into contact with oxygenates, comprises a contact surface of at least one of said component.

9. A process according to claim 1, wherein the oxygenate feedstock is reacted to produce the olefinic product in the presence of an olefinic co-feed.

10. A process according to claim 1, wherein the oxygenate conversion catalyst comprises a molecular sieve having one-dimensional 10-membered ring channels.

* * * * *